United States Patent
Suzuki et al.

(10) Patent No.: US 9,789,277 B2
(45) Date of Patent: Oct. 17, 2017

(54) HOUSING TOOL

(71) Applicant: TERUMO KABUSHIKI KAISHA, Shibuya-ku (JP)

(72) Inventors: Kenta Suzuki, Fujinomiya (JP); Hiroshi Yagi, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/563,548

(22) Filed: Dec. 8, 2014

(65) Prior Publication Data
US 2015/0094693 A1   Apr. 2, 2015

Related U.S. Application Data

(63) Continuation of application No. PCT/JP2013/056717, filed on Mar. 12, 2013.

(30) Foreign Application Priority Data

Jul. 19, 2012   (JP) .................................. 2012-160397

(51) Int. Cl.
  *B65D 69/00*   (2006.01)
  *A61M 25/00*   (2006.01)
  *A61M 25/09*   (2006.01)

(52) U.S. Cl.
  CPC .... *A61M 25/002* (2013.01); *A61M 25/09041* (2013.01)

(58) Field of Classification Search
  CPC ....................... A61M 25/002; A61M 25/09041
  (Continued)

(56) References Cited

U.S. PATENT DOCUMENTS 4,332,322 A * 6/1982 Jaeschke ............. A61M 25/002
                                                 206/363
5,947,296 A * 9/1999 Castora ................ A61B 19/026
                                                 206/364
(Continued)

FOREIGN PATENT DOCUMENTS

CN           1933867 A    3/2007
CN         102264427 A   11/2011
(Continued)

OTHER PUBLICATIONS

International Search Report (PCT/ISA/210) mailed on Jun. 11, 2013, by the Japan Patent Office as the International Searching Authority for International Application No. PCT/JP2013/056717.
(Continued)

*Primary Examiner* — J. Gregory Pickett
*Assistant Examiner* — Jenine Pagan
(74) *Attorney, Agent, or Firm* — Buchanan Ingersoll & Rooney PC

(57) ABSTRACT

A housing tool suppresses rotation of a tubular body in a winding direction that holds an elongated medical body in a packaging body, and suppresses deformation of a distal end portion of the elongated medical body. The housing tool includes a tube-shaped holder that is wound in a circular shape for holding a guide wire, a fastening member that fixes adjacent portions of the wound holder, and a mounting member that includes engagement portions and to be engaged with the fastening member, reaches an outer side of a circle of the holder wound in a circular shape, and covers an end portion of the holder from which the guide wire is derived.

20 Claims, 7 Drawing Sheets

(58) Field of Classification Search
USPC .................................... 206/364, 571, 570
See application file for complete search history.

(56) References Cited

U.S. PATENT DOCUMENTS

| | | | |
|---|---|---|---|
| 6,053,313 A | 4/2000 | Farrell et al. | |
| 7,328,794 B2* | 2/2008 | Lubs .................... | A61M 25/002 206/364 |
| 7,334,678 B2* | 2/2008 | Kesler ................. | A61M 25/002 206/303 |
| 7,549,270 B2* | 6/2009 | Rowe .................. | A61M 25/002 206/364 |
| 7,640,714 B2* | 1/2010 | Waller ................. | A61M 25/002 206/364 |
| 7,815,045 B2* | 10/2010 | Delaney .............. | A61M 25/002 206/363 |
| 9,022,212 B2* | 5/2015 | Spaargaren ......... | A61B 19/026 206/364 |
| 2004/0055919 A1* | 3/2004 | Rowe .................. | A61M 25/002 206/438 |
| 2005/0061698 A1 | 3/2005 | Delaney et al. | |
| 2007/0185413 A1 | 8/2007 | Asai et al. | |
| 2007/0197998 A1 | 8/2007 | Itou et al. | |
| 2012/0022470 A1 | 1/2012 | Kuniyasu et al. | |
| 2012/0261290 A1* | 10/2012 | Limjaroen ......... | A61M 25/002 206/364 |
| 2014/0144798 A1* | 5/2014 | Benesh .............. | B65D 73/0021 206/363 |

FOREIGN PATENT DOCUMENTS

| | | |
|---|---|---|
| EP | 0 782 868 A1 | 7/1997 |
| EP | 0 913 164 A1 | 5/1999 |
| JP | 09-201369 A | 8/1997 |
| JP | 2001-505449 A | 4/2001 |
| JP | 2006-006782 A | 1/2006 |
| JP | 2008-012196 A | 1/2008 |
| JP | 4280526 B2 | 6/2009 |
| WO | WO 98/18515 A1 | 5/1998 |
| WO | 2005/087304 A1 | 9/2005 |

OTHER PUBLICATIONS

European Search Report issued Feb. 12, 2016, by the European Patent Office, in corresponding European Patent Application No. 13820065.4 (6 pages).

Office Action (Notification of the First Office Action) issued on Nov. 17, 2015, by the Patent Office of the People's Republic of China in corresponding Chinese Application No. 201380021913.5, and an English translation of the Office Action. (13 pages).

Office Action (Notification of Second Office Action) issued on May 6, 2016, by the Patent Office of the People's Republic of China in corresponding Chinese Patent Application No. 201380021913.5, and an English translation of the Office Action. (13 pages).

Office Action (Notice of Reasons for Rejection) dated Oct. 11, 2016 issued by the Japanese Patent Office in corresponding Japanese Patent Application No. 2014-525729, and English language translation of Office Action (7 pages).

Communication pursuant to Article 94(3) EPC issued Jul. 14, 2016, by the European Patent Office, in corresponding European Patent Application No. 13820065.4. (5 pages).

Third Office Action dated Jul. 19, 2016 issued by the Patent Office of the People's Republic of China in corresponding Chinese Patent Application No. 201380021913.5, and English language translation of Office Action (8 pages).

* cited by examiner

[FIG. 1]
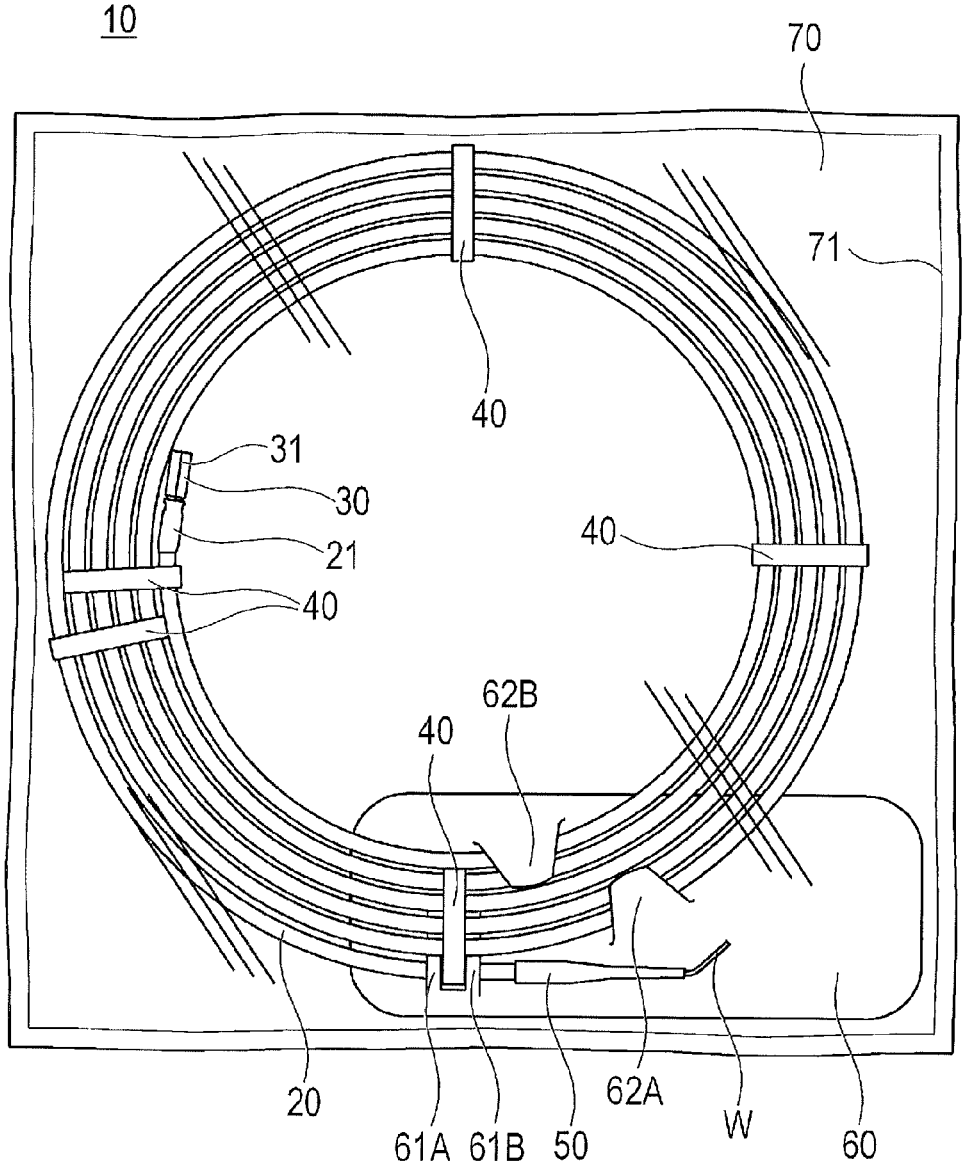

[FIG. 2]
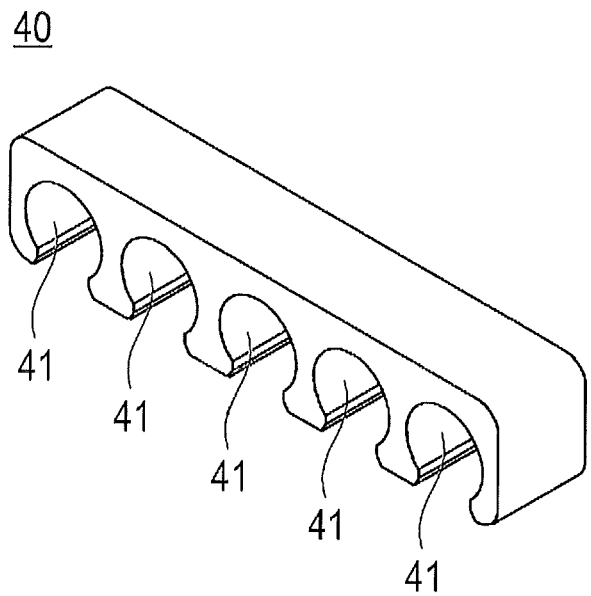
[FIG. 3]
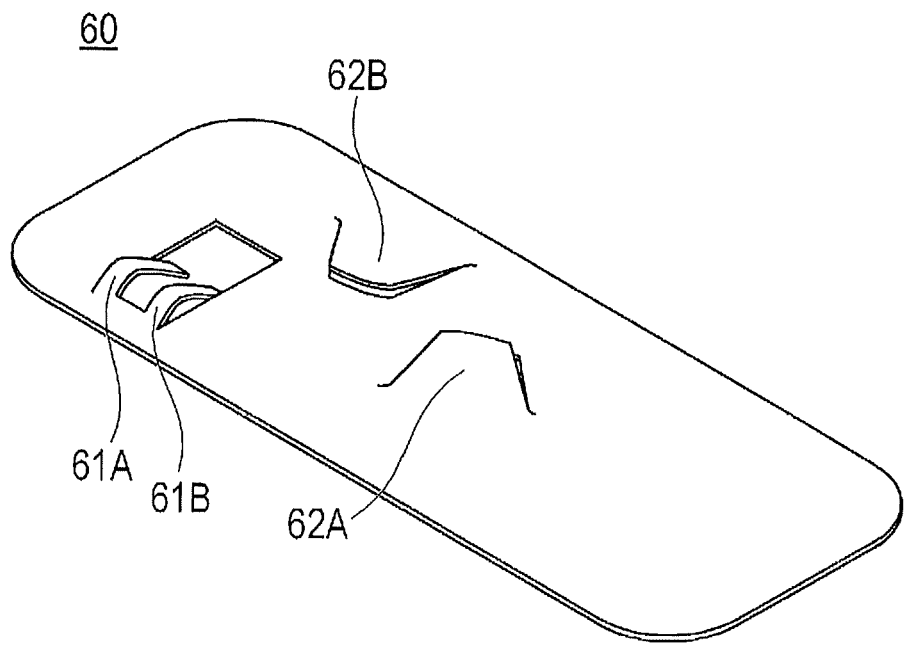

[FIG. 4]
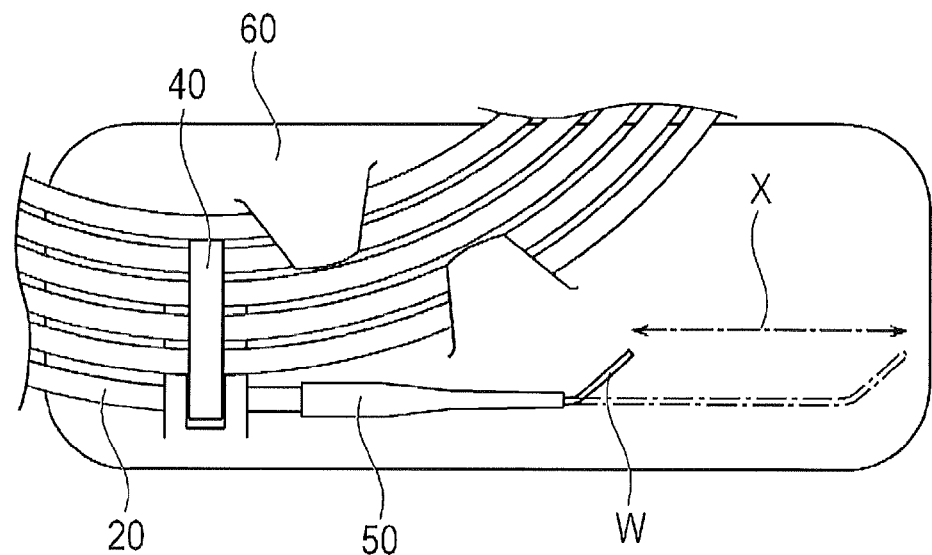
[FIG. 5]
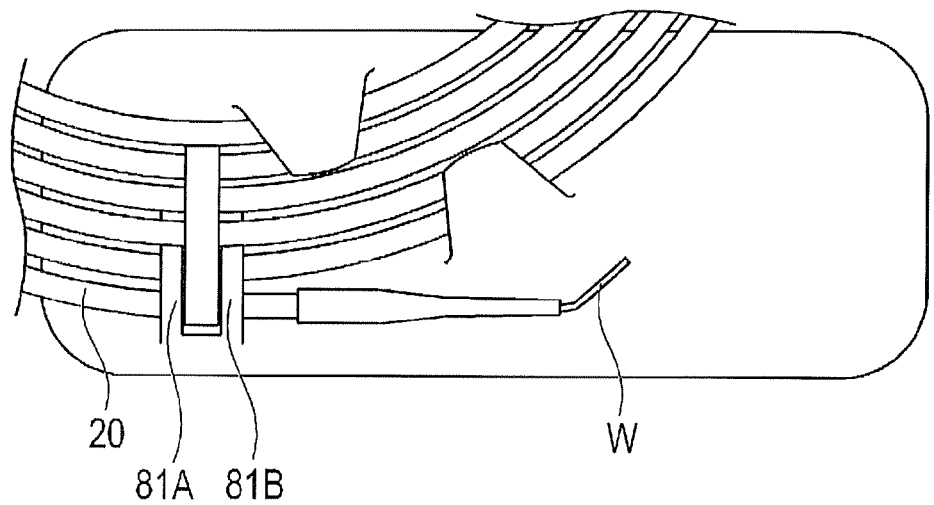

[FIG. 6]
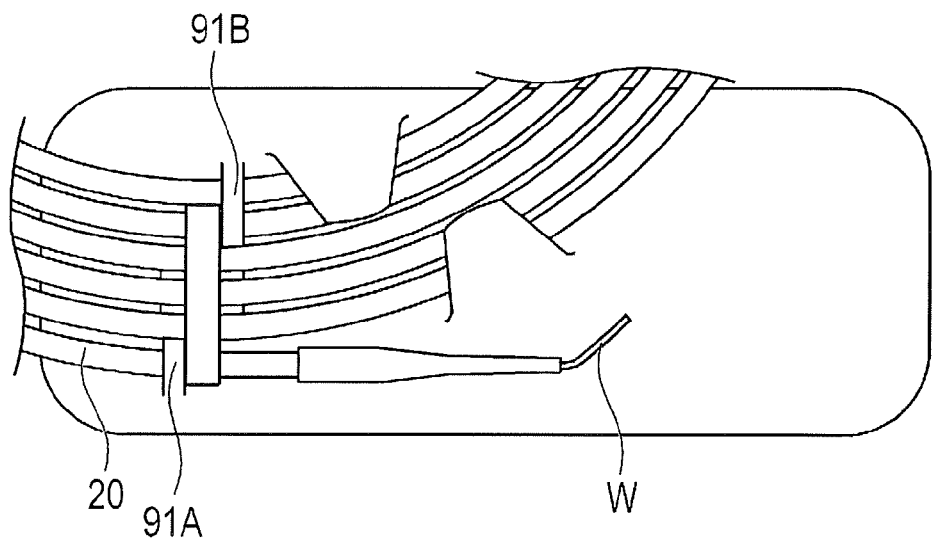
[FIG. 7]
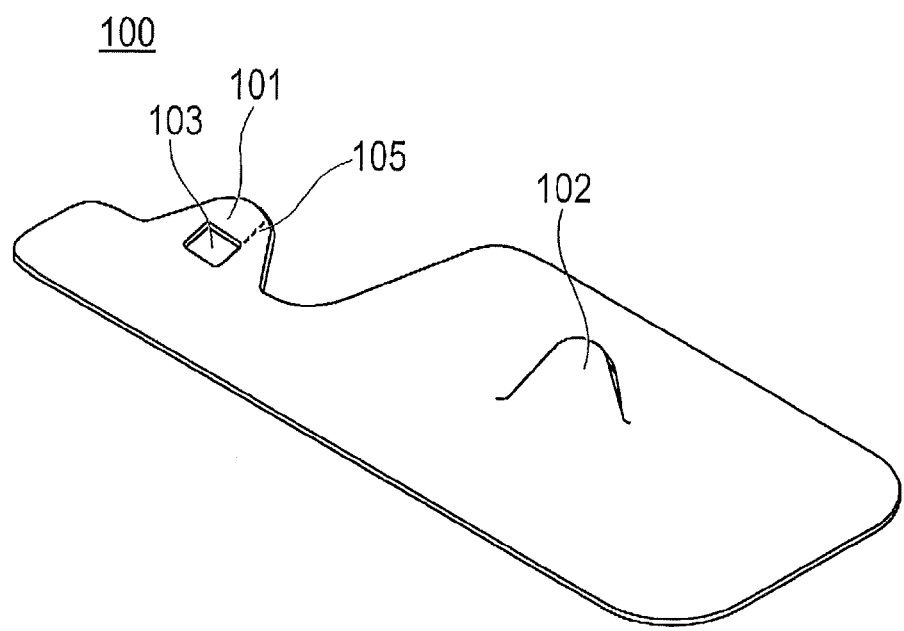

[FIG. 8]
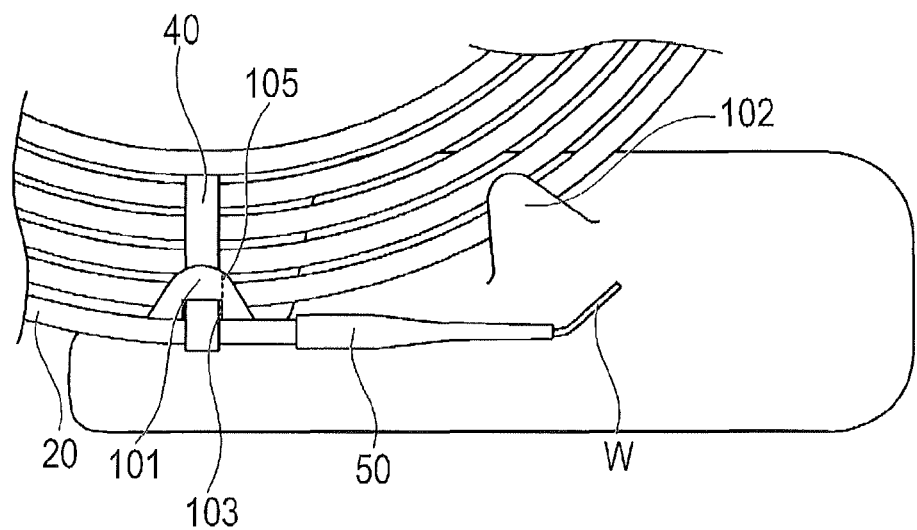
[FIG. 9]
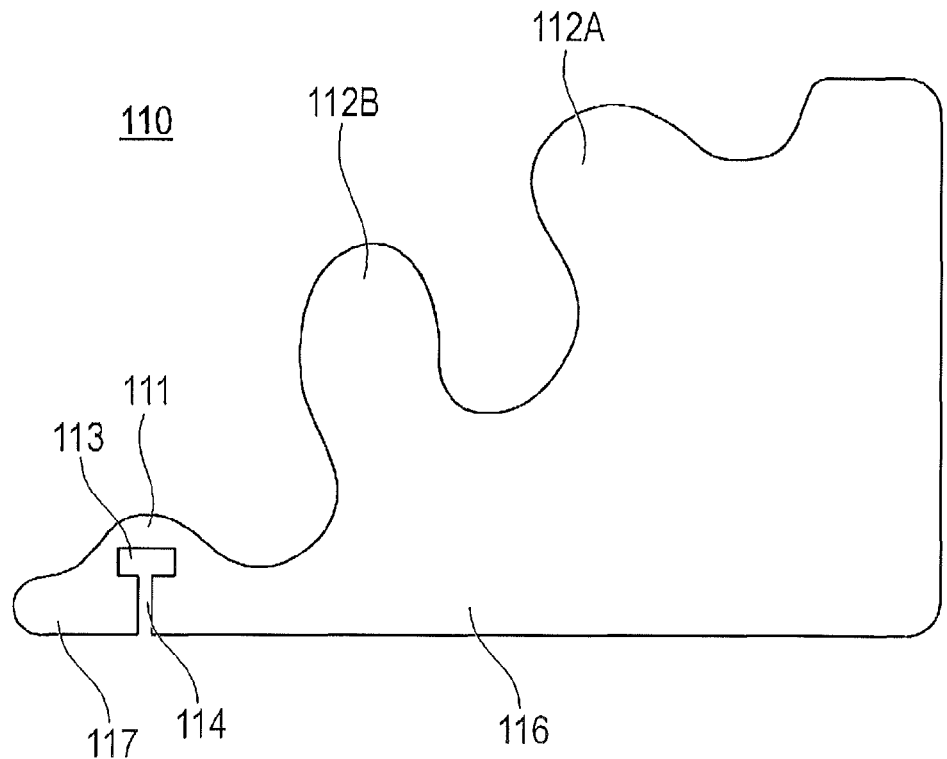

[FIG. 10]
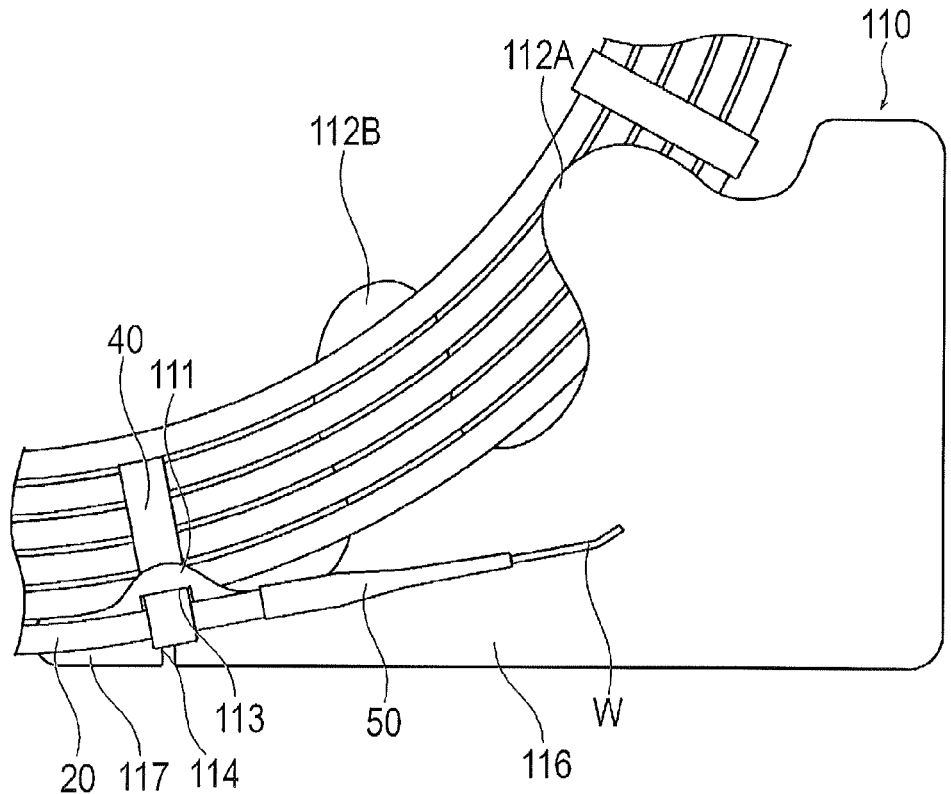
[FIG. 11]
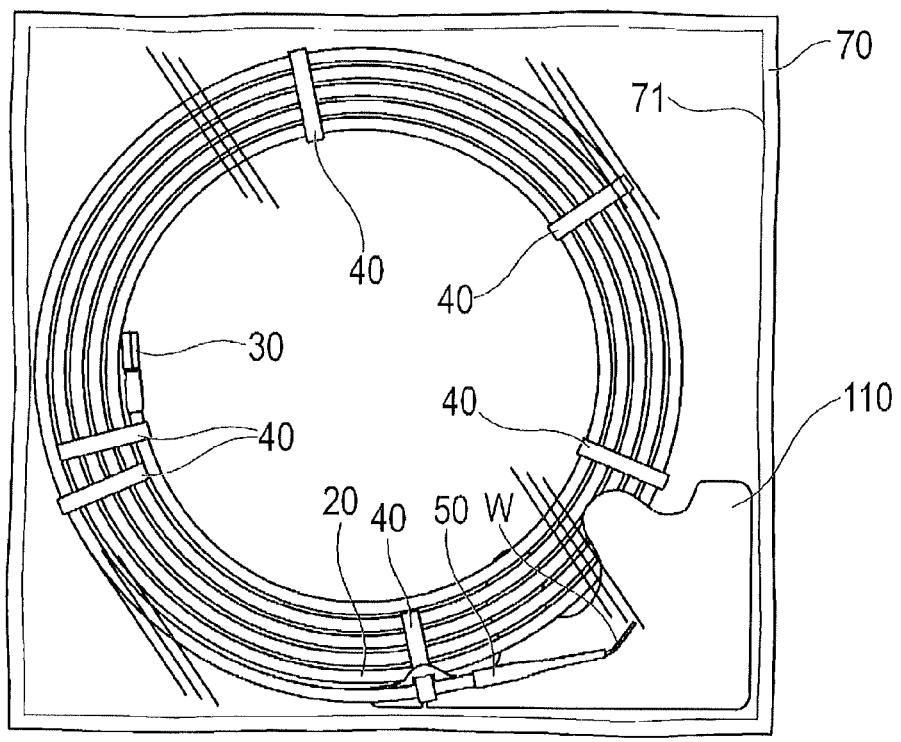

[FIG. 12]
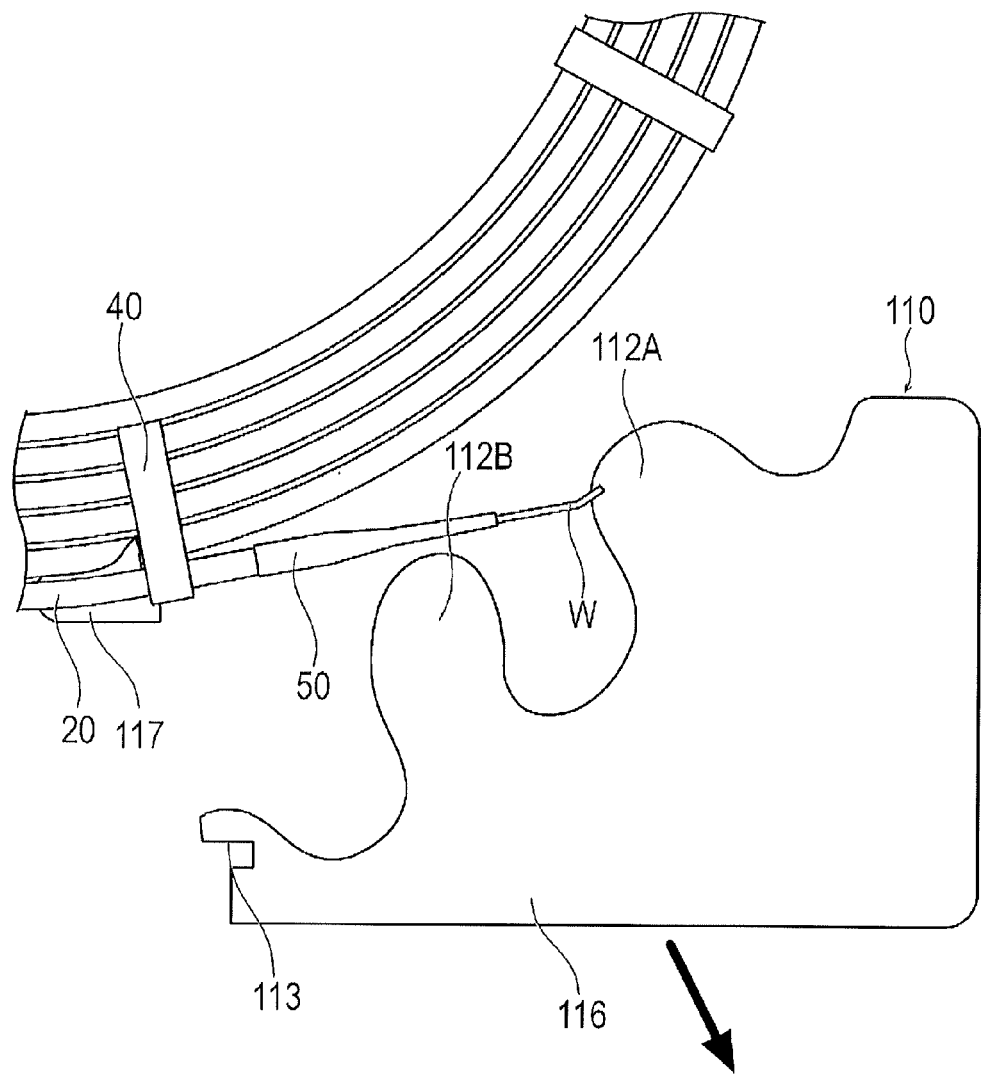

HOUSING TOOL

CROSS-REFERENCES TO RELATED APPLICATIONS

This application is a continuation of International Application No. PCT/JP2013/056717 filed on Mar. 12, 2013, and claims priority to Japanese Application No. 2012-160397 filed on Jul. 19, 2012, the entire content of both of which is incorporated herein by reference.

TECHNICAL FIELD

The present invention generally relates to a housing tool that holds an elongated medical body.

BACKGROUND DISCUSSION

Recently, a technique of inserting a catheter into a lumen such as a blood vessel to administer drug solution such as a contrast agent or an anticancer drug or to insert and implant a stent through the catheter has been performed. At this time, generally, a guide wire precedes in the lumen, and the catheter is inserted to a target position along the guide wire.

The guide wire is generally held in a housing tool having a certain shape, to be stored and conveyed. For example, in Japanese Application Publication No. 2006-6782, a housing tool for a guide wire in which the shape of a holder which is a tubular body wound in a circular shape is maintained by a fastening tool is disclosed. In the housing tool, an inserter for assisting an operation of inserting a guide wire into a catheter is connected to a distal end portion of a holder, and the guide wire is held so that the distal end portion of the guide wire protrudes from the inserter, and the entire content is packaged in a packaging body for maintaining a sterilized state. A part of the holder has small curvature radius, and the protrusion of the guide wire is suppressed by the frictional resistance in this portion.

SUMMARY

However, even if the guide wire is held in the housing tool, the guide wire may be unintentionally deformed by the rotation of the tubular body wound in a circular shape in the winding direction in the packaging body, or the protrusion of the distal end portion of the guide wire from the inserter owing to an impact or a vibration at the time of conveyance.

Disclosed here is a housing tool that can suppress the rotation of the tubular body in the winding direction in the packaging body, and that can suppress the deformation of the distal end portion of the elongated medical body held in the tubular body.

According to an aspect, a housing tool includes an elongated tubular body that is wound in a circular shape for holding an elongated medical body; a fastening member that fixes radially adjacent portions of the wound tubular body to each other; and a mounting member that includes an engagement portion to be engaged with the fastening member. The mounting member extends outwardly beyond an outer periphery of an outermost winding of the wound tubular body, and covers an end portion of the tubular body from which the elongated medical body projects from the tubular body.

In the housing tool configured as described above, since the mounting member reaches the outer side of the circle of the tubular body wound in a circular shape, the mounting member comes into contact with the inner edge of the packaging body in the packaging body so that the rotation of the tubular body in the winding direction can be suppressed. Furthermore, since the mounting member covers the end portion of the tubular body from which the elongated medical body is derived, even if the elongated medical body is packaged with the packaging body, it is possible to prevent the distal end portion of the elongated medical body from coming in contact with the inner edge of the packaging body.

If the engagement portion is engaged with the fastening member to interpose the fastening member from two sides in a winding direction of the tubular body, the rotation of the tubular body in the winding direction can be favorably suppressed.

If the engagement portion is inserted between adjacent portions of the wound tubular body, and has a hole portion which the fastening member penetrates, it is possible to rather easily and securely attach the engagement portion to the fastening member by a simple operation of inserting the fastening member into the hole portion.

If the hole portion is formed to be continuous from a border portion of the mounting member, it is possible to dispose the fastening member from the border portion of the mounting member to the hole portion so that the engagement portion can be relatively easily engaged with the fastening member.

If the mounting member further includes an auxiliary engagement portion that is engaged with the tubular body, the engagement between the mounting member and the tubular body is caused to be strong so that when the tubular body is packaged with the packaging body, the rotation of the tubular body in the packaging body can be more securely suppressed.

If the mounting member covers an entire part of the elongated medical body derived from the tubular body, when the elongated medical body is packaged with the packaging body, it is possible to securely prevent the elongated medical body from coming into contact with the inner edge of the packaging body.

If the mounting member covers only a part of the tubular body, a favorable ejection property from the packaging body can be maintained without increasing the volume of the mounting member in the packaging body.

If an elongated medical body is held in the housing body and packaged, since the rotation of the tubular body in the winding direction in the packaging body is suppressed, the contact of the elongated medical body with the packaging body is suppressed so that the deformation of the distal end portion of the elongated medical body derived from the tubular body can be suppressed.

According to another aspect, a housing tool includes: an elongated tubular body in which is positioned an elongated medical body, a fastening member mounted on the tubular body, and a mounting member mounted on the tubular body. The elongated medical body is removable from the tubular body, and the tubular body and the elongated medical body inside the tubular body are helically wound so that the wound tubular body includes portions that are radially adjacent one another. The wound tubular body possesses a radially outermost winding and also possesses an end portion from which projects a portion of the elongated medical body. The fastening member is mounted on the holder so that the fastening member fixes a plurality of the radially adjacent portions of the wound tubular body to each other. The mounting member includes a sheet-shaped part extending outwardly beyond the outer periphery of the radially outermost winding of the wound tubular body. The mounting member includes an engagement portion on opposite sides of the fastening member that hold the fastening member. The mounting member and a portion of the wound tubular body overlie one another, and the mounting member and the end portion of the tubular body overlie one another.

In accordance with another aspect, a housing tool comprises an elongated tubular body in which is positioned an elongated guide wire, a fastening member, and a mounting member mounted on the helically wound tubular body. The guide wire is removable from the tubular body and includes one end portion projecting outwardly from the elongated tubular body at one end of the elongated medical body. The tubular body and the guide wire inside the tubular body are helically wound so that the wound tubular body includes portions that are radially adjacent one another. The fastening member engages a plurality of the radially adjacent portions of the wound tubular body, and the includes a sheet-shaped part extending outwardly beyond the outer periphery of the radially outermost winding of the wound tubular body. The mounting member includes an engagement portion on opposite sides of the fastening member that holds the fastening member, with the mounting member and a portion of the wound tubular body overlying one another, and the mounting member and the end of the tubular body overlying one another. The housing tool also includes packaging in which the wound tubular body, the guide wire, the mounting member and the fastening member are positioned in a sterilized state. The packaging has an inner side, and the sheet-shaped part of the mounting member is configured to suppress rotation of the wound tubular body in the packaging by virtue of contact between the sheet-shaped part of the mounting member and the inner side of the packaging.

BRIEF DESCRIPTION OF DRAWINGS

FIG. 1 is a plan view illustrating a housing tool according to an embodiment representing one example of the housing tool disclosed here.

FIG. 2 is a perspective view illustrating a fastening member.

FIG. 3 is a perspective view illustrating a mounting member.

FIG. 4 is a plan view illustrating a state when a guide wire protrudes from a holder.

FIG. 5 is a plan view illustrating a modification example of the mounting member.

FIG. 6 is a plan view illustrating another modification example of the mounting member.

FIG. 7 is a perspective view illustrating still another modification example of the mounting member.

FIG. 8 is a plan view illustrating a housing tool to which the mounting member illustrated in FIG. 7 is applied.

FIG. 9 is a plan view illustrating still another modification example of the mounting member.

FIG. 10 is a plan view illustrating a state when the mounting member illustrated in FIG. 9 is attached to the holder.

FIG. 11 is a plan view illustrating a state when the mounting member illustrated in FIG. 10 is held in a packaging body.

FIG. 12 is a plan view illustrating a state when the mounting member illustrated in FIG. 10 is removed from the holder.

DETAILED DESCRIPTION

Hereinafter, an embodiment of the housing tool constituting an example of the housing tool disclosed here is described with reference to the accompanying drawings. Further, ratios of dimensions in the drawings may be exaggerated for simplicity of description and may be different from the actual ratios.

A housing tool 10 according to the present embodiment holds a guide wire W in order to store and convey (e.g., transport) the guide wire W (elongated medical body) as illustrated in FIG. 1. The housing tool 10 includes a tube-shaped holder 20 (tubular body) in which is held the guide wire W, a connector 30 that holds a proximal end portion of the guide wire W and connects the proximal end portion of the guide wire W to a proximal end portion of the holder 20, fastening members 40 that are attached to the holder 20 to maintain the shape of the holder 20, an inserter 50 (tubular body) that is connected to a distal end portion of the holder 20, a mounting member 60 that is attached to the distal end portion of the holder 20, and a packaging body (packaging) 70 in which the holder 20, the connector 30, the fastening members 40 and the inserter 50 are held in a sterilized state. The holder 20 is helically wound so that portions of the holder are radially adjacent one another. Further, the distal end portion of the holder 20 is an external end portion of the wound holder 20 (i.e., the distal end portion of the holder 20 is located on the radially outer side of the wound holder), and the proximal end portion of the holder 20 is an internal end portion of the wound holder 20 (i.e., the proximal end portion of the holder 20 is located on the radially inner side of the wound holder). The holder 20 and the inserter 50 are connected to each other so that they are configured as one tubular body.

The inserter 50 is tube-shaped and possesses an outer diameter that decreases toward the distal end. The inserter 50 is attached to the distal end portion of the holder 20, protects the distal end portion of the guide wire W, and also guides the guide wire W when the guide wire W is inserted into a catheter.

The guide wire W held in the holder 20 can be a well-known guide wire. For example, a guide wire obtained by covering a core wire made from stainless steel or a superelastic alloy (Ni—Ti) with a synthetic resin such as polyethylene, polyvinyl chloride, polyester polypropylene, polyamide, polyurethane, polystyrene, polycarbonate, a fluorine-based resin (PTFE or ETFE), or various kinds of elastomer can be used, but materials and configurations are not particularly limited.

A tube that extends a certain length is wound a plurality of times (five or six times in the present embodiment) as the holder 20 to generally form a spiral shape. A hub portion 21 is formed on the proximal end portion of the holder 20 and is inside the spiral (i.e., is at the radially inner side of the holder). Materials forming the holder 20 are not particularly limited, but a polyolefin such as polyethylene, polypropylene, an ethylene-propylene copolymer, or an ethylene-vinyl acetate copolymer, polyvinyl chloride, polystyrene, polyamide, polyimide, or the like can be applied.

The connector 30 is tube-shaped and includes a longitudinally extending slit 31. The connector 30 holds the guide wire W inside through the slit 31, is inserted into the hub portion 21 of the holder 20, and is connected to the holder 20 so that the proximal end portion of the guide wire W is interposed and held by elastic force. Materials forming the connector 30 are not particularly limited, and a polyolefin such as polyethylene, polypropylene, or an ethylene-propylene copolymer, or various resin materials such as polyvinyl chloride, polystyrene, polyamide, polycarbonate, and an acrylic resin can be applied, but it is preferable to use relatively soft material so as to be elastically deformed.

The fastening members 40 are provided at a plurality of spaced apart positions in a circumferential direction (winding direction) of the holder 20, and fix the adjacent portions of the tube to be parallel to each other. As illustrated in FIG. 2, the fastening member 40 includes concave portions or grooves 41 for holding the holder 20. The concave portions or grooves are provided side by side, and the fastening member 40 is connected to the holder 20 by pushing the holder 20 into the concave portions 41 so that the spiral shape of the holder 20 is maintained. Materials forming the fastening members 40 are not particularly limited, and a polyolefin such as polyethylene, polypropylene, or an ethylene-propylene copolymer, or various resin materials such as polyvinyl chloride, polystyrene, polyamide, polycarbonate, and an acrylic resin can be used.

The mounting member 60 is formed by one sheet of sheet-shaped cardboard, and includes a pair of circumferentially spaced apart and parallel engagement portions 61A and 61B (projecting portions) between which is interposed or located one of the fastening members 40 provided near the distal end portion of the holder 20. The engagement portions 61A and 61B are engaged with the fastening member 40. The mounting member 60 also includes spaced apart auxiliary engagement portions 62A and 62B that engage and overlie several of the radially adjacent windings of the holder 20 on one side (upwardly facing side in FIG. 1) of the holder 20. The mounting member 60 supports a region of the distal end portion of the holder 20 from one surface side (rear surface side of FIG. 1). The mounting member 60 possesses a rectangular shape, and the four corners of the rectangular-shaped mounting member 60 are cut to be rounded so that the packaging body 70 is not damaged.

The respective engagement portions 61A and 61B are configured to possess a claw shape, cover a part of the outermost tube portion (winding) of the holder 20 wound in the spiral shape, and are inserted or positioned between the outermost tube portion and the tube portion (winding) inside the outermost tube portion (winding) so as to be engaged with the fastening member 40. Since the pair of engagement portions 61A and 61B interposes the fastening member 40 from both sides in the winding direction of the wound holder 20, the movement of the holder 20 in a radial direction is limited and the movement in the winding direction is also limited.

The auxiliary engagement portion 62A on one side possesses a claw shape, and covers a portion (several radially adjacent windings) of the tube from the external side of the spiral shape of the holder 20, and the auxiliary engagement portion 62B on the other side possesses a claw shape, and covers a portion (several radially adjacent windings) of the tube from the internal side of the spiral shape of the holder 20. Accordingly, the pair of auxiliary engagement portions 62A and 62B limits the movement of the holder 20 in the radial direction.

The mounting member 60 may be configured and sized to overlie or cover the entire part of the guide wire W protruding distally beyond the holder 20 and the inserter 50 (i.e., the distal end portion of the guide wire W), while also overlying or covering the distal end portion of both the holder 20 and the inserter 50 as illustrated in, for example, FIG. 1. In this embodiment, the mounting member 60 is positioned in one of the four corners of the packaging body 70 so that the mounting member 60 occupies only a part of the internal space in the packaging body 70. As shown for example in FIG. 1, two parts of the tube-shaped holder 20 (tubular body), which are diametrically opposite to one another, are each uncovered by the mounting member 60 over a respective radial extent of the tube-shaped holder 20 from the radially innermost winding to the radially outermost winding. The mounting member 60 can also be larger in size so as to cover the entire holder 20. In such an embodiment, the mounting member 60 would extend across the entire internal space in the packaging body 70. As illustrated in FIG. 4, the mounting member 60 covers a range X in which the guide wire W protrudes from the inserter 50 when an impact or vibration is applied to the housing tool 10. Further, with respect to the movement of the guide wire W in the axial direction, since the guide wire W is merely fixed with the connector 30 on the proximal end side of the holder 20, the guide wire W can relatively easily protrude beyond the distal-most end of the inserter 50 owing to the existence of slack in the holder 20.

The material forming the mounting member 60 is paper, but the mounting member 60 is not particularly limited to this material, and a polyolefin such as polyethylene, polypropylene, an ethylene-propylene copolymer, or an ethylene-vinyl acetate copolymer, polyvinyl chloride, polystyrene, polyamide, polyimide, or the like can be used.

The packaging body 70 holds or encloses the holder 20 as well as the guide wire W located in the holder 20, and also holds or encloses the connector 30 and the inserter 50 which are connected to the holder 20, and the mounting member 60 which covers or overlies a part of the holder 20. The packaging body 70 holds all of these parts 20, W, 30, 50, 60 in a sterilized state inside the packaging body 70. The packaging body 70 possesses a rectangular shape, and the mounting member 60 is sized and configured to be disposed in one of the four corners of the internal space in the packaging member 70 or is sized and configured to cover the entire internal space in the packaging member 70. An inner edge (side) 71 formed on the outermost portion of the internal space of the packaging body 70 can come into contact with the mounting member 60. Next, the operation of the housing tool 10 according to the present embodiment is described.

In the housing tool 10 according to the present embodiment, since the mounting member 60 reaches the external side of the circle of the holder 20 which is wound in a circular shape, the mounting member 60 comes into contact with the inner edge (side) 71 of the packaging body 70 in the packaging body 70 so that the rotation of the tubular body in the winding direction is suppressed. That is, the mounting member 60 extends outwardly beyond the outer periphery of the holder 20 and is configured in such a way that the holder 20 is inhibited from rotating because the mounting member 60 contacts the inner edge of the packaging body 70. If the holder 20 rotates in the winding direction, the guide wire W that is held by the holder 20 can contact the inner edge 71 of the packaging body 70 and can be easily bent, but since the rotation is suppressed, the deformation of the distal end portion of the guide wire W can be suppressed. Additionally, since the guide wire W is not easily brought into contact with the packaging body 70, the damage to the packaging body 70 can be reduced. Furthermore, since the mounting member 60 covers (overlaps with or overlies) the end portion of the tubular body configured with the holder 20 and the inserter 50 from which the guide wire W is derived, even if the guide wire W is packaged with the packaging body 70, the distal end portion of the guide wire W can be prevented from being brought into contact with the inner edge 71 of the packaging body 70 of the guide wire W. Therefore, even if an impact or vibration is applied to the housing tool 10, the rotation of the holder 20 in the winding direction in the packaging body 70 is suppressed, and the deformation of the distal end portion of the guide wire W is suppressed.

Additionally, since the engagement portions 61A and 61B interpose the fastening member 40 from both sides in the winding direction of the holder 20, and are engaged with the fastening member 40, it is possible to favorably suppress the rotation of the holder 20 in the winding direction.

Additionally, when the mounting member 60 is attached to the holder 20, after the holder 20 is fixed by the fastening members 40, the mounting member 60 is attached to the holder 20 wound in a spiral shape so that it is not required to wind and fix the holder 20 to the mounting member 60 simultaneously and the workability is rather high.

Additionally, since the present embodiment does not have the configuration of suppressing the protrusion of the guide wire W using frictional resistance by reducing the curvature radius of a portion of the wound holder 20, the ejection resistance of the guide wire W does not increase, and it is difficult for the guide wire W to be bent.

Additionally, the mounting member 60 covers the range X in which the guide wire W protrudes from the inserter 50 if an impact or vibration is applied to the housing tool 10, so the deformation of the distal end portion of the guide wire W can be more securely suppressed.

Additionally, since the mounting member 60 further includes the auxiliary engagement portions 62A and 62B that are engaged with the holder 20, the engagement of the holder 20 with the mounting member 60 is stronger, so when the guide wire W is packaged with the packaging body 70, the movement of the holder 20 in the packaging body 70 is more securely suppressed so that the deformation of the distal end portion of the guide wire W can be suppressed.

Additionally, since the mounting member 60 covers the entire part of the guide wire W which is derived from the holder 20, the deformation of the distal end portion of the guide wire W can be suppressed by suppressing the contact of the guide wire W with the packaging body 70.

Additionally, since the mounting member 60 covers only a portion of the holder 20, a favorable ejection property from the packaging body 70 can be maintained without increasing the volume of the mounting member 60 in the packaging body 70, so packaging processes are relatively easy and packaging costs can be reduced.

The present invention is not limited to the embodiments described above, and various modifications are possible by a person having ordinary skill in the art without departing from the technical idea of the present invention. For example, as illustrated in FIG. 5, a pair of circumferentially spaced apart and parallel engagement portions 81A and 81B (projecting portions) may hold two or more radially adjacent tube portions of the holder 20.

Additionally, as illustrated in FIG. 6, a pair of circumferentially and radially spaced apart and parallel engagement portions 91A and 91B (projecting portions) may hold and interpose the wound holder 20 from the inner side and from the outer side. Thus, one of the engagement portions 91A on one side of the fastening member 40 is positioned on the outer side of the wound holder 20 and projects radially inwardly, and the other engagement portion 91B on the other side of the fastening member 40 is positioned on the inner side of the wound holder 20 and projects radially outwardly.

Additionally, as illustrated in FIGS. 7 and 8, a mounting member 100 may include an engagement portion 101 in which is located a hole portion 103 which the fastening member 40 penetrates, and an auxiliary engagement portion 102 engaged with the holder 20. The auxiliary engagement portion 102 is claw-shaped, covers or overlies the tube from the outside of the spiral-shaped holder 20, and limits the movement of the holder 20 in the radial direction. The engagement portion 101 is configured, by virtue of the hole portion 103, so that parts of the engagement portion 101 are positioned on opposite sides of the fastening member with the fastening member between and in contact with parts of the engagement portion 101. The engagement portion 101 is claw-shaped on the border portion of the mounting member 100, is inserted between two tubes on the outermost circumference side of the holder 20 from one surface side (rear surface side of FIG. 8), and the fastening member 40 penetrates the hole portion 103. For this engagement, the portion of the tube on the outermost circumference side among the radially adjacent portions of the tube of the holder 20 connected to the fastening member 40 is released from the fastening member 40, the engagement portion 101 is inserted between the radially adjacent portions of the tube, the fastening member 40 is inserted into the hole portion 103, and the portion of the tube released from the fastening member 40 is inserted again into the fastening member 40 to be connected. Accordingly, the fastening member 40 is securely held to be interposed from both sides in the winding direction of the holder 20 by the engagement portion 101 so that the movement of the holder 20 in the radial direction is limited and the movement in the winding direction is also limited. In this manner, the engagement portion 101 can be rather easily and securely attached by a simple operation of inserting the fastening member 40 into the hole portion 103, and also the engagement of the engagement portion 101 is stronger than the configuration of only hooking, so that the deformation of the distal end portion of the guide wire W is more securely suppressed. Further, the engagement portion 101 may be inserted between two radially adjacent portions of the other than two radially adjacent portions on the outermost circumference side of the holder 20.

A fragile portion 105 that is broken to release the hole of the hole portion 103 may be formed in the engagement portion 101 to extend from the border portion of the mounting member 100 to the hole portion 103. The fragile portion 105 is formed by, for example, perforation, a groove, or a notch and is broken by dragging the mounting member 100 so that the fastening member 40 held by the hole portion 103 is released from the hole portion 103. Accordingly, the mounting member 100 can be relatively easily released from the holder 20. Further, the fragile portion 105 may not necessarily be formed.

Additionally, the auxiliary engagement portions 62A and 62B may not be provided. Further, the mounting member may cover or overlie the entire holder 20, not only a portion of the holder 20. Additionally, the configuration of the engagement portion is not limited as long as the engagement portion can be engaged with the fastening member 40, and for example, the engagement portion may have a shape of a clip that interposes the fastening member 40 by elastic force. Additionally, the mounting member need not have a sheet shape.

Additionally, various kinds of information may be written on the mounting member. The written information includes a size of the guide wire W, or an instruction at the time of using the guide wire W. Additionally, the various kinds of information may be directly printed on the mounting member, or information printed in advance may be attached to the mounting member. Additionally, for example, a torque device for assisting a rotation operation of the guide wire or a mandrel for shaping a distal end may be attached to a blank portion of the mounting member.

Additionally, according to the present embodiment, one tubular body is formed by the holder 20 and the inserter 50, but the tubular body may be configured with only the holder, without installing the inserter 50. Additionally, the housing tool may hold other medical elongated bodies such as a balloon catheter or a microcatheter, in addition to the guide wire.

Additionally, in the same manner as in the modification example illustrated in FIG. 9, a mounting member 110 may include an engagement portion 111 having a hole portion 113 which the fastening member 40 penetrates, and auxiliary engagement portions 112A and 112B that are engaged with the holder 20. The engagement portion 111 is configured, by virtue of the hole portion 113, so that parts of the engagement portion 111 are positioned on opposite sides of the fastening member with the fastening member between and in contact with parts of the engagement portion 111. The hole portion 113 is continuous with (opens to) the border portion or outer periphery of the mounting member 110 by a cut portion or slit 114 extending from the hole portion 113 to the border portion or the outer periphery of the mounting member 110. With respect to the mounting member 110, a first part 116 having the auxiliary engagement portions 112A and 112B is positioned on one side of the cut portion 114, and a second part 117 having a smaller size dimension (and area) than that of the first part 116 is positioned on the other side of the cut portion 114 so that the cut portion is interposed between the first larger part 116 and the second smaller part 117. One of the auxiliary engagement portions 112A is located on one side (top side in FIG. 10) of the wound holder 20 while the other auxiliary engagement portion 112B is positioned on the opposite side (bottom side in FIG. 10) of the wound holder 20 that the holder 20 is held between the two auxiliary engagement portions 112A and 112B. The auxiliary engagement portions 112A and 112B are formed in a claw shape and are configured as protruding portions of the mounting member 110 that protrude outwardly away from the remainder of the mounting member 110. As seen in FIG. 9, the border portion of the mounting member 110 possesses an uneven or undulating configuration, with protruding parts of the border portion corresponding to the auxiliary engagement portions. Both of the auxiliary engagement portions 112A, 112B cover the holder 20 from the outer side of the spiral shape of the holder 20 since both of the auxiliary engagement portions protrude from the same side of the border portion of the mounting member 110.

The material and the dimension of the mounting member 110 are not particularly limited, and the mounting member 110 may be formed from a sheet made of low foam polyethylene.

As illustrated in FIG. 10, with respect to the mounting member 110, between two radially adjacent portions of the wound tube on the outermost circumference side of the holder 20, the engagement portion 111 is engaged with the holder 20 by using the cut portion 114 so that the fastening member 40 is inserted into the hole portion 113. Accordingly, the movements of the holder 20 in the winding direction and the radial direction are suppressed. Then, an auxiliary engagement portion 112B on one hand covers the tube on the rear surface side from the outer side of the spiral shape of the holder 20, and an auxiliary engagement portion 112A on the other hand covers the front surface side of the tube from the outer side of the spiral shape of the holder 20. Accordingly, the movement of the holder 20 in the radial direction can be effectively suppressed.

As illustrated in FIG. 11, the holder 20 holding the guide wire W, the connector 30, the inserter 50, and the mounting member 110 are held in the packaging body 70. According to the present embodiment, since the mounting member 110 reaches the outer side of the circle of the holder 20 wound in a circular shape (i.e., the mounting member 110 extends outwardly beyond the outermost winding of the wound holder 20), the mounting member 110 comes into contact with the inner edge (side) 71 of the packaging body 70 in the packaging body 70, and the rotation of the holder 20 in the winding direction is suppressed.

When the mounting member 110 is removed from the holder 20, after the packaging body 70 is opened and the content is ejected or removed, as illustrated in FIG. 12, the auxiliary engagement portions 112A and 112B which cover the holder 20 from the outer side in the radial direction are rather easily separated from the holder 20 by drawing the mounting member 110 to the outer side of the holder 20 in the radial direction, and the second part 117 is separated from the first part 116 by tearing off the mounting member 110 at the hole portion 113 so that the mounting member 110 can be relatively easily removed from the holder 20. Further, a fragile portion formed with, for example, perforation, a groove, or a notch may be formed in the engagement portion 111 so that the mounting member 110 can be more easily torn. Additionally, the mounting member 110 may be removed from the holder 20 so as not to be torn.

In this manner, according to the mounting member 110 illustrated in FIGS. 9 to 12, since the hole portion 113 is formed to be continuous from the border portion by the cut portion 114 extending from the border portion of the mounting member 110, the engagement portion 111 is rather easily engaged with the fastening member 40 without removing the tube of the holder 20 from the fastening member 40. Also, the fastening member 40 is securely held to be interposed from both sides in the winding direction of the holder 20 by the engagement portion 111, so the movement of the holder 20 in the radial direction is limited, and the movement in the winding direction is also limited. Further, the engagement portion 111 may be inserted between two portions of the tube other than the two portions of the tube on the outermost circumference side of the holder 20. Additionally, the auxiliary engagement portion 112B may cover the front surface side of the holder 20 instead of covering the front surface side of the holder 20 with the auxiliary engagement portion 112A.

The detailed description above describes embodiments of a housing tool representing examples of the housing tool disclosed here. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A housing tool comprising:
an elongated tubular body that is wound to form a wound tubular body and configured to hold an elongated medical body such that the elongated medical body projects outwardly beyond an end portion of the wound tubular body, the wound tubular body including a radially outermost winding and a radially innermost winding;
a fastening member that fixes radially adjacent portions of the wound tubular body to each other;

a mounting member that includes an engagement portion to be engaged with the fastening member, the engagement portion including a hole portion through which the fastening member passes;

the mounting member covering a first part of the wound tubular body, inclusive of the end portion of the wound tubular body, the mounting member extending outwardly beyond an outer periphery of a part of the radially outermost winding of the wound tubular body, the mounting member covering less than the entirety of the wound tubular body so that a part of the radially innermost winding of the wound tubular body is uncovered by the mounting member; and second and third parts of the tubular body each being uncovered by the mounting member over a respective radial extent of the tubular body from the radially innermost winding to the radially outermost winding, the second and third parts being diametrically opposite to one another.

2. The housing tool according to claim 1, wherein the engagement portion is positioned between adjacent portions of the wound tubular body.

3. The housing tool according to claim 1, wherein the hole portion opens to a border portion of the mounting member.

4. The housing tool according to claim 1, wherein the mounting member further includes an auxiliary engagement portion that is engaged with the tubular body.

5. An elongated medical body that is held in the housing tool according to claim 1, including packaging in which the elongated tubular body, the fastening member and the mounting member are positioned.

6. A housing tool comprising:

an elongated tubular body that is wound to form a wound tubular body and configured to hold an elongated medical body such that the elongated medical body projects outwardly beyond an end portion of the wound tubular body, the wound tubular body including a radially outermost winding and a radially innermost winding;

a fastening member that fixes radially adjacent portions of the wound tubular body to each other;

a mounting member that includes an engagement portion to be engaged with the fastening member, the engagement portion being engaged with the fastening member on opposite sides of the fastening member in a winding direction of the tubular body such that the fastening member is interposed between portions of the engagement portion;

the mounting member covering a first part of the wound tubular body, inclusive of the end portion of the wound tubular body, the mounting member extending outwardly beyond an outer periphery of a part of the radially outermost winding of the wound tubular body, the mounting member covering less than the entirety of the wound tubular body so that a part of the radially innermost winding of the wound tubular body is uncovered by the mounting member; and second and third parts of the tubular body each being uncovered by the mounting member over a respective radial extent of the tubular body from the radially innermost winding to the radially outermost winding, the second and third parts being diametrically opposite to one another.

7. The housing tool according to claim 6, wherein the engagement portion includes first and second spaced apart projecting portions that project in opposite directions.

8. The housing tool according to claim 6, wherein the fastening member passes through the engagement portion so that respective spaced apart regions of the engagement portion on the opposite sides of the fastening member engage the opposite sides of the fastening member.

9. A housing tool comprising:

an elongated tubular body in which is positioned an elongated medical body, the elongated medical body being removable from the tubular body, the tubular body and the elongated medical body inside the tubular body being wound so that the wound tubular body includes portions that are radially adjacent one another, the wound tubular body possessing a radially outermost winding and a radially innermost winding, the tubular body possessing an end portion from which projects a portion of the elongated medical body;

a fastening member mounted on the wound tubular body so that the fastening member fixes a plurality of the radially adjacent portions of the wound tubular body to each other;

a mounting member mounted on the wound tubular body, the mounting member including a sheet-shaped part extending outwardly beyond an outer periphery of the radially outermost winding of the wound tubular body, the mounting member comprising an engagement portion including a through hole, the fastening member passing through the through hole;

the mounting member and a portion of the wound tubular body overlying one another, and the mounting member and the end portion of the tubular body overlying one another; and a first part of the radially innermost winding of the wound tubular body and the mounting member do not overlie one another, and a second part of the radially innermost winding of the wound tubular body and the mounting member do not overlie one another, the first and second parts being diametrically opposite to one another.

10. The housing tool according to claim 9, wherein the engagement portion includes a slit extending from the through hole to an outer periphery of the sheet-shaped mounting member.

11. The housing tool according to claim 9, wherein the mounting member further comprises at least one auxiliary engagement portion that overlies a plurality of the radially adjacent windings of the wound tubular body.

12. The housing tool according to claim 9, wherein the mounting member further comprises two auxiliary engagement portions that each overlie at least a portion of one of the windings of the wound tubular body.

13. The housing tool according to claim 12, wherein one of the auxiliary engagement portions projects radially outwardly and the other auxiliary engagement portions projects radially inwardly.

14. The housing tool according to claim 9, wherein the wound tubular body possesses oppositely facing sides, at least a portion of one of the sides of the wound tubular body being in contact with the engagement portion, and wherein the mounting member further comprises two auxiliary engagement portions, one of the auxiliary engagement portions overlying one of the sides of the wound tubular body and the other auxiliary engagement portion overlying the other side of the wound tubular body.

15. A housing tool comprising:

an elongated tubular body in which is positioned an elongated medical body, the elongated medical body being removable from the tubular body, the tubular body and the elongated medical body inside the tubular body being wound so that the wound tubular body includes portions that are radially adjacent one another, the wound tubular body possessing a radially outermost winding and a radially innermost winding, the tubular body possessing an end portion from which projects a portion of the elongated medical body;

a fastening member mounted on the wound tubular body so that the fastening member fixes a plurality of the radially adjacent portions of the wound tubular body to each other;

a mounting member mounted on the wound tubular body, the mounting member including a sheet-shaped part extending outwardly beyond an outer periphery of the radially outermost winding of the wound tubular body, the engagement portion including two circumferentially spaced apart projecting portions in contact with opposite sides of the fastening member;

the mounting member and a portion of the wound tubular body overlying one another, and the mounting member and the end portion of the tubular body overlying one another; and a first part of the radially innermost winding of the wound tubular body and the mounting member do not overlie one another, and a second part of the radially innermost winding of the wound tubular body and the mounting member do not overlie one another, the first and second parts being diametrically opposite to one another.

16. The housing tool according to claim 15, wherein the two circumferentially spaced apart projecting portions are radially spaced apart and project in opposite directions.

17. A housing tool comprising:

an elongated tubular body in which is positioned an elongated guide wire, the guide wire being removable from the tubular body and including one end portion projecting outwardly from the elongated tubular body at one end of the elongated tubular body, the tubular body and guide wire inside the tubular body being wound so that the wound tubular body includes portions that are radially adjacent one another, the wound tubular body possessing a radially outermost winding, the wound tubular body also possessing oppositely facing first and second surfaces;

a fastening member engaging a plurality of the radially adjacent portions of the wound tubular body;

a mounting member mounted on the wound tubular body, the mounting member including a sheet-shaped part extending outwardly beyond an outer periphery of the radially outermost winding of the wound tubular body;

the mounting member and less than an entirety of the wound tubular body overlying one another so that the first surface of a first part of the wound tubular body faces the mounting member while the first surface of a second part of the wound tubular body and the first surface of a third part of the wound tubular body do not face the mounting member, the second and third parts of the wound tubular body including a part of the innermost winding of the wound tubular body, the second and third parts being diametrically opposite to one another, and the mounting member and the end of the tubular body overlying one another; and packaging in which the wound tubular body, the guide wire, the mounting member and the fastening member are positioned in a sterilized state, the packaging including an inner side, and the sheet-shaped part of the mounting member being configured to suppress rotation of the wound tubular body in the packaging by virtue of contact between the sheet-shaped part of the mounting member and the inner side of the packaging.

18. The housing tool according to claim 17, wherein the mounting member further comprises at least one auxiliary engagement portion that overlies a plurality of the radially adjacent windings of the wound tubular body.

19. The housing tool according to claim 17, wherein the mounting member further comprises two circumferentially spaced apart auxiliary engagement portions that each overlie at least a portion of one of the windings of the wound tubular body.

20. The housing tool according to claim 17, wherein the wound tubular body possesses oppositely facing sides, at least a portion of one of the sides of the wound tubular body being in contact with the sheet-shaped part of the mounting member, and wherein the mounting member further comprises two auxiliary engagement portions, one of the auxiliary engagement portions overlying one of the sides of the wound tubular body and the other auxiliary engagement portion overlying the other side of the wound tubular body.

* * * * *